US008200501B2

(12) United States Patent
Friedlander et al.

(10) Patent No.: US 8,200,501 B2
(45) Date of Patent: Jun. 12, 2012

(54) METHODS, SYSTEMS AND COMPUTER PROGRAM PRODUCTS FOR SYNTHESIZING MEDICAL PROCEDURE INFORMATION IN HEALTHCARE DATABASES

(75) Inventors: Robert R. Friedlander, Southbury, CT (US); James R. Kraemer, Santa Fe, NM (US)

(73) Assignee: International Business Machines Corporation, Armonk, NY (US)

( * ) Notice: Subject to any disclaimer, the term of this patent is extended or adjusted under 35 U.S.C. 154(b) by 1228 days.

(21) Appl. No.: 11/339,931

(22) Filed: Jan. 26, 2006

(65) Prior Publication Data
US 2007/0174090 A1    Jul. 26, 2007

(51) Int. Cl.
*G06Q 10/00* (2006.01)
(52) U.S. Cl. .......................................................... 705/2
(58) Field of Classification Search .................. 705/2, 3, 705/4
See application file for complete search history.

(56) References Cited

U.S. PATENT DOCUMENTS

| | | |
|---|---|---|
| 4,328,978 A | 5/1982 | McLaughlin |
| 5,991,758 A | 11/1999 | Ellard |
| 6,024,699 A | 2/2000 | Surwit et al. |
| 6,058,391 A | 5/2000 | Gardner |
| 6,189,004 B1 | 2/2001 | Rassen et al. |
| 6,212,524 B1 | 4/2001 | Weissman et al. |
| 6,377,993 B1 | 4/2002 | Brandt et al. |
| 6,385,604 B1 | 5/2002 | Bakalash et al. |
| 6,397,224 B1 | 5/2002 | Zubeldia et al. |
| 6,509,898 B2 | 1/2003 | Chi et al. |
| 6,578,043 B2 | 6/2003 | Nye |
| 6,629,106 B1 | 9/2003 | Narayanaswamy et al. |
| 6,636,850 B2 | 10/2003 | Lepien |
| 6,714,979 B1 | 3/2004 | Brandt et al. |
| 6,941,311 B2 | 9/2005 | Shah et al. |
| 6,978,268 B2 | 12/2005 | Thomas et al. |
| 6,996,567 B2 | 2/2006 | Ghukasyan |
| 7,035,849 B2 | 4/2006 | Tifft |
| 7,080,081 B2 | 7/2006 | Agarwal et al. |
| 7,107,155 B2 | 9/2006 | Frudakis |
| 7,111,010 B2 | 9/2006 | Chen |
| 7,191,183 B1 | 3/2007 | Goldstein |
| 2002/0083075 A1* | 6/2002 | Brummel et al. ............. 707/102 |

(Continued)

FOREIGN PATENT DOCUMENTS

JP    2002312373 A    10/2002

(Continued)

OTHER PUBLICATIONS

Adam et al., "Positive Patient Identification: a Practical Solution to a Challenging Problem," Toward an Electronic Patient '97. Conference and Exposition. Proceedings, Pt. vol. 3, pp. 100-108, 1997.

(Continued)

*Primary Examiner* — Vivek Koppikar
*Assistant Examiner* — Edward Winston, III
(74) *Attorney, Agent, or Firm* — Yudell Isidore Ng Russell PLLC (57) ABSTRACT

Methods, systems and computer program products for synthesizing medical procedure information stored in healthcare databases are provided. A medical procedure query associated with a single patient or a group of patients is received. Query results are provided responsive to the medical procedure query. The query results may include medical procedures from multiple sources that are expressed in multiple standards formats.

21 Claims, 5 Drawing Sheets

U.S. PATENT DOCUMENTS

| | | | |
|---|---|---|---|
| 2002/0099691 A1 | 7/2002 | Lore et al. | |
| 2002/0156791 A1 | 10/2002 | Nesamoney et al. | |
| 2003/0074222 A1 | 4/2003 | Rosow et al. | |
| 2003/0088438 A1* | 5/2003 | Maughan et al. | 705/2 |
| 2003/0126148 A1 | 7/2003 | Gropper et al. | |
| 2003/0126156 A1 | 7/2003 | Stoltenberg et al. | |
| 2003/0171876 A1 | 9/2003 | Markowitz | |
| 2003/0191699 A1 | 10/2003 | Deveault et al. | |
| 2004/0064449 A1 | 4/2004 | Ripley et al. | |
| 2004/0073458 A1* | 4/2004 | Jensen | 705/2 |
| 2004/0111298 A1 | 6/2004 | Schoenberg | |
| 2004/0181433 A1* | 9/2004 | Blair | 705/2 |
| 2004/0181526 A1 | 9/2004 | Burdick et al. | |
| 2004/0220829 A1* | 11/2004 | Baharav et al. | 705/2 |
| 2004/0220836 A1 | 11/2004 | Doherty et al. | |
| 2005/0182722 A1 | 8/2005 | Meyer et al. | |
| 2005/0246189 A1 | 11/2005 | Monitzer et al. | |
| 2006/0041450 A1 | 2/2006 | Dugan | |

FOREIGN PATENT DOCUMENTS

| | | |
|---|---|---|
| JP | 2002342484 A | 11/2002 |
| WO | WO 96/27163 | 9/1996 |
| WO | WO 01/08077 A1 | 2/2001 |
| WO | WO01/37097 A1 | 5/2001 |

OTHER PUBLICATIONS

Chatfield, "Marketing an HMO by 'Smart' ID Cards with Patient History on an Electronic Medical Record," Proceedings. Toward an Electronic Patient Record '96. Twelfth International Symposium on the Creation of Electronic Health Record System and Global Conference on Patient Cards, Pt. vol. 1, pp. 608-620, 1996.

Gabrieli, "Guide for Unique Healthcare Identifier Model," *Journal of Clinical Computing*, vol. 21, No. 5, pp. 101-139, 1993.

Goehring, "Identification of Patients in Medical Databases—Soundex Codes Versus Match Code," *Medical Informatics*, vol. 10, No. 1, pp. 27-34, Jan.-Mar. 1985.

Goodwin, Linda et al., "Data Mining for Preterm Birth Prediction," Proceedings of the 2000 ACM Symposium on Applied Computing (Mar. 19-21,2000—Como, Italy), vol. 1, pp. 46-51pp. 46-51.

Grimson et al., "The SI Challenge in Health Care," *Communications of the ACM*, vol. 43, No. 6, Jun. 2000, pp. 49-55.

Hoshiai et al., "SION Architecture: Semantic Information-Oriented Network Architecture," *Transactions of the Institute of Electronics, Information and Communication Engineers B.*, vol. J84-B, No. 3, pp. 411-424, Mar. 2001.

Kim et al. "A Solution to the Distribution and Standardization of Multimedia Medical Data in E-Health" *ACM International Conference Proceeding Series 147 Proceedings of the Pan-Sydney area workshop on Visual Information processing*11 161-164 (2001).

Lowery et al., "Barriers to Implementing Simulation in Health Care," Proceedings from the 1994 Winter Simulation Conference, pp. 868-875.

Phillips Jr. et al. "Person-Matching by Electronic Methods" *Communications of the ACM* 5(7):404-407 (1962).

Polak et al., "Using Automated Analysis of the Resting Twelve-Lead ECG to Identify Patients at Risk of Developing Transient Myocardial Ischaemia—an Application of an Adaptive Logic Network," *Physiological Measurement*, vol. 18, No. 4, pp. 317-325, Nov. 1997.

Shelfer et al., "Smart Card Evolution," *Communications of the ACM*, vol. 45, No. 7, Jul. 2002, pp. 83-88.

Wang, C., "A COBRA-based Object Framework with Patient Identification Translation and Dynamic Linking. Methods for Exchanging Patient Data," *Methods of Information in Medicine*, vol. 38, No. 1, pp. 56-65, Mar. 1999.

Zarowski et al., "Some Algorithms for Circadian Rhythm Identification," 2001 IEEE Pacific Rim Conference on Communications, Computers, and Signal Processing, Pt. vol. 2, pp. 425-428, 2001.

* cited by examiner

METHODS, SYSTEMS AND COMPUTER PROGRAM PRODUCTS FOR SYNTHESIZING MEDICAL PROCEDURE INFORMATION IN HEALTHCARE DATABASES

FIELD OF THE INVENTION

The invention relates to database management in general and, more particularly, to synthesizing to data stored in databases.

BACKGROUND OF THE INVENTION

As the field of healthcare continues to become more specialized, the provision of services by many healthcare workers and/or providers to one patient and/or many patients may increase. In order to accomplish this, healthcare delivery has been organized into specialized departments or healthcare sources such as, for example, nursing, laboratory, pharmacy, and radiology departments. Each department has the responsibility for accomplishing its particular, often specialized, subset of tasks. Sometimes the departments are associated with different healthcare enterprises or offices having different geographic locations. Unfortunately, this has resulted in sub-optimal healthcare operations because patient information related to a single patient that is stored at various departments may not be easily accessible from a single place.

This patient information, or medical data, may be stored in a database environment configured to store large volumes of data. Furthermore, the medical data stored in the database environment may be processed by, for example, searching the stored medical data. Details with respect to conventional methods for storing and/or accessing medical data in and/or from databases is discussed in, for example, United States Patent Publication Nos. US 2003/0088438 and US 2003/0177132.

The patient information, for example, medical procedure information, may be stored using one of many standards, such as clinical procedure treatment (CPT) standard, healthcare common procedure coding system (HCPCS), and the like. Thus, synthesizing this patient information into coherent pictures may be difficult because the same information may be called something different in each database. Furthermore, as the amount of available medical data expands, it may become increasingly difficult to synthesize the medical data, especially for research and comparison purposes. For example, use of the medical data for purposes of diagnosing/treating various medical conditions and/or researching medical areas may be very difficult.

SUMMARY OF THE INVENTION

Some embodiments of the present invention provide methods, systems and computer program products for synthesizing medical procedure information stored in healthcare databases. A medical procedure query associated with a single patient or a group of patients is received. Query results are provided responsive to the medical procedure query. The query results may include medical procedures from multiple sources that are expressed in multiple standards formats.

In further embodiments of the present invention a username and password associated with the username may be verified. In these embodiments, the medical procedure query may only be received if the username and password are verified. Each username and associated password may be associated with a level of security clearance. The level of security clearance may determine which information can be accessed by a user of the associated username and password.

It still further embodiments of the present invention, it may be determined if the medical procedure query includes a first standards code in conformance with a first standard therein. Equivalent standards codes to the first standards code in conformance with at least one second standard, different from the first standard, may be determined if it is determined that the medical procedure query includes a first standards code. The query results may be provided based on both the first standards code and the equivalent standards codes.

In some embodiments of the present invention, query adjustments may be received responsive to the provided query results. Future query results may be adjusted based on the received query adjustments. The received medical procedure query may include a discrete query or a semantic query.

In further embodiments of the present invention, the received medical procedure query may be processed to generate at least one modified medical procedure query that can be provided to external databases to obtain the query results. The at least one modified medical procedure query may be provided to at least one standards database and/or at least one medical procedure results database. Intermediate query results may be received from the at least one standards database and/or the at least one medical procedure results database. A format of the intermediate query results may be modified before the query results are provided to a user. The format may be modified based on a user profile and/or information obtained from previously received medical procedure queries.

DETAILED DESCRIPTION OF EMBODIMENTS OF THE INVENTION

The invention now will be described more fully hereinafter with reference to the accompanying drawings, in which illustrative embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout. As used herein, the term "and/or" includes any and all combinations of one or more of the associated listed items.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/ or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

As will be appreciated by one of skill in the art, the invention may be embodied as a method, data processing system, or computer program product. Accordingly, the present invention may take the form of an entirely hardware embodiment, an entirely software embodiment or an embodiment combining software and hardware aspects all generally referred to herein as a "circuit" or "module." Furthermore, the present invention may take the form of a computer program product on a computer-usable storage medium having computer-usable program code embodied in the medium. Any suitable computer readable medium may be utilized including hard disks, CD-ROMs, optical storage devices, a transmission media such as those supporting the Internet or an intranet, or magnetic storage devices.

Computer program code for carrying out operations of the present invention may be written in an object oriented programming language such as Java®, Smalltalk or C++. However, the computer program code for carrying out operations of the present invention may also be written in conventional procedural programming languages, such as the "C" programming language or in a visually oriented programming environment, such as VisualBasic.

The program code may execute entirely on the user's computer, partly on the user's computer, as a stand-alone software package, partly on the user's computer and partly on a remote computer or entirely on the remote computer. In the latter scenario, the remote computer may be connected to the user's computer through a local area network (LAN) or a wide area network (WAN), or the connection may be made to an external computer (for example, through the Internet using an Internet Service Provider).

The invention is described in part below with reference to flowchart illustrations and/or block diagrams of methods, systems, computer program products and data structures according to embodiments of the invention. It will be understood that each block of the illustrations, and combinations of blocks, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the block or blocks.

These computer program instructions may also be stored in a computer-readable memory that can direct a computer or other programmable data processing apparatus to function in a particular manner, such that the instructions stored in the computer-readable memory produce an article of manufacture including instruction means which implement the function/act specified in the block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the block or blocks.

Embodiments of the present invention will now be discussed with respect to FIGS. 1 through 6. As discussed herein, some embodiments of the present invention provided methods, systems and computer program products for synthesizing medical procedures of one or more patients. The medical procedure information may be stored in healthcare databases in different locations. In particular, a researcher or medical personnel may provide a medical procedure query associated with a single patient or a group of patients to a healthcare query module according to some embodiments of the present invention. As used herein, a "medical procedure query" may include any information related to medical procedures performed on a single patient or group of patients for medical treatment/diagnosis and/or research purposes. According to some embodiments of the present invention, query results may be provided, responsive to the medical procedure query. The query results may include synthesized medical procedures for one or more patients from multiple sources/records that are expressed in multiple standards formats as will be discussed further below with respect to FIGS. 1 through 6.

Figure 1:
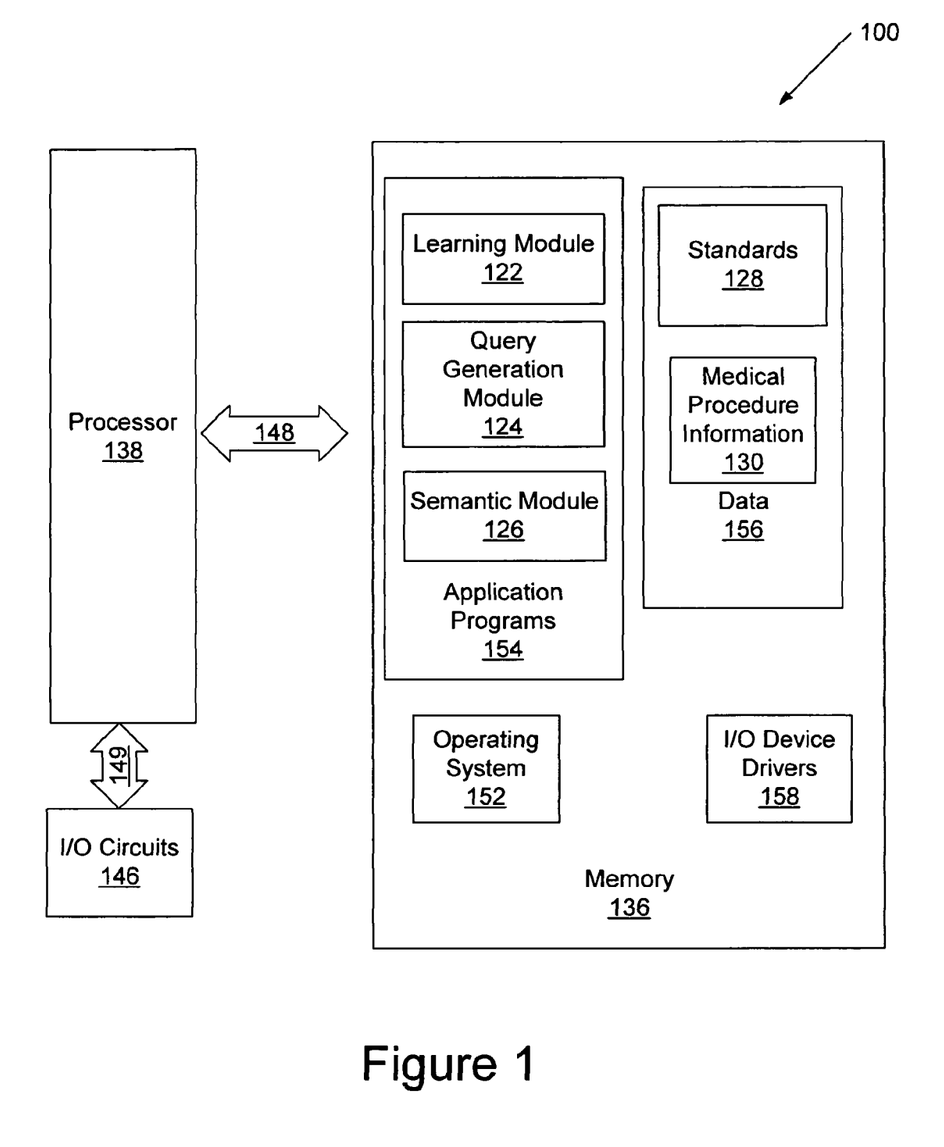
FIG. 1 is a block diagram illustrating data processing systems according to some embodiments of the present invention.

Referring now to FIG. 1, an exemplary data processing system 100 or healthcare query module/database environment that may be included in devices operating in accordance with some embodiments of the present invention will be discussed. As illustrated, the data processing system 100 includes a processor 138, a memory 136 and input/output circuits 146. The data processing system 100 may be incorporated in, for example, a personal computer, server, router or the like. The processor 138 communicates with the memory 136 via an address/data bus 148 and communicates with the input/output circuits 146 via an address/data bus 149. The input/output circuits 146 can be used to transfer information between the memory 136 and another computer system or a network using, for example, an Internet Protocol (IP) connection. These components may be conventional components such as those used in many conventional data processing systems, which may be configured to operate as described herein.

In particular, the processor 138 can be any commercially available or custom microprocessor, microcontroller, digital signal processor or the like. The memory 136 may include any memory devices containing the software and data used to implement the functionality circuits or modules used in accordance with embodiments of the present invention. The memory 136 can include, but is not limited to, the following types of devices: cache, ROM, PROM, EPROM, EEPROM, flash memory, SRAM, DRAM and magnetic disk. In some embodiments of the present invention, the memory 136 may be a content addressable memory (CAM).

As further illustrated in FIG. 1, the memory 136 may include several categories of software and data used in the data processing system 100: an operating system 152; application programs 154; input/output device drivers 158; and data 156. As will be appreciated by those of skill in the art, the operating system 152 may be any operating system suitable for use with a data processing system, such as OS/2, AIX or zOS from International Business Machines Corporation, Armonk, N.Y., Windows95, Windows98, Windows2000 or WindowsXP from Microsoft Corporation, Redmond, Wash., Unix or Linux. The input/output device drivers 158 typically include software routines accessed through the operating system 152 by the application programs 154 to communicate with devices such as the input/output circuits 146 and certain memory 136 components. The application programs 154 are illustrative of the programs that implement the various features of the circuits and modules according to some embodiments of the present invention. Finally, the data 156 represents the static and dynamic data used by the application programs 154, the operating system 152, the input/output device drivers 158, and other software programs that may reside in the memory 136. As illustrated in FIG. 1, the data 156 may include standards 128 and medical procedure results 130 for use by the circuits and modules of the application programs 154 according to some embodiments of the present invention as discussed further herein.

As used herein, "standards" 128 refer to medical standards, such as clinical procedure treatment (CPT) standard, healthcare common procedure coding system (HCPCS) and the like, local institution standards, insurance company codes/standards as well as any information that may be published in medical journal articles and the like. In particular, a single medical procedure may be associated with several different codes. For example, a medical professional may chose one code for the patient's chart. However, hospital personnel may change the code for the procedure on the insurance form, as a second code, for the same procedure, may allow the patient, medical professional and/or hospital to receive more money from the insurance company. This procedure may be referred to as up-coding. The opposite of up-coding is down-coding, which is the reassembly of procedure codes to minimize the payment to providers. Furthermore, local institutions may have their own subset of standards that may specifically deal with things that they encounter more often than other institutions. For example, a cancer hospital may have more detailed standards codes for different procedures because they see more cancer patients than other hospitals. Furthermore, the standards 128 may also include old standard protocols and names that have now been superceded so that older medical procedures may also be included in results provided according to some embodiments of the present invention as will be discussed further herein. As used herein, "medical procedure information" 130 may include information related to medical procedures performed on one or more patients and the results thereof, such as lab results, pathology reports, images (x-rays, MRIs etc.), physician's notes, and the like. The medical procedure information 130 may include both discrete data and semantic data without departing from the scope of the present invention.

Referring again to FIG. 1, according to some embodiments of the present invention the application programs 154 include a semantic module 126, a query generation module 124 and a learning module 122. The semantic module 126 may be configured to receive a medical procedure query from an external source, for example, a computing device being operated by a researcher or medical personnel. The semantic module 126 may be configured to receive medical procedure queries in multiple languages. In some embodiments of the present invention, the user (researcher or medical personnel) may be assigned a unique username and password. In these embodiments of the present invention, the semantic module 126 may be further configured to verify the user name and password before the user is allowed to make a medical procedure query. In some embodiments of the present invention, the username and password may be associated with a level of security clearance. Thus, each username and password may define what records a user making a medical procedure query can access. This can be used to keep highly confidential information in only a few hands. In some embodiments of the present invention, the security feature may be used to limit access to ones coworker's records. For example, a username and password of a nurse working at a particular hospital may indicate that this nurse cannot access the records of other employees at the same hospital. Thus, people's private information can be kept confidential from their coworkers.

The medical procedure query may be, for example, a discrete query or a semantic query. A discrete query may be, for example, a specific question such as "show me all patients who have had a mammogram over the past ten years." The medical procedure "mammogram" may be expressed using a standards code for mammogram, for example, it may be expressed in HCPCS. A semantic query may be more complicated and may require more processing to determine exactly what is being asked as will be discussed further below.

For example, when the semantic module 126 receives a discrete medical procedure query like the example above, the semantic module 126 may be configured to provide the discrete medical procedure query to the query generation module 124. The query generation module 124 may be configured to determine what the code for mammogram is in all current and past medical standards. Then, all of the healthcare databases may be searched for each of the codes and the results may be provided to the query generation circuit 124. The query generation circuit 124 may provide the query results to the user making the medical procedure query.

In some embodiments of the present invention, the query generation circuit 124 may be configured to provide the query results to the semantic module 126 before the results are provided to the user. For example, if the results are more complicated than just patients who have had a mammogram, the semantic module 126 may be configured to organize the query results and present them to the user in more user friendly format. For example, as discussed above, some embodiments of the present invention require a user name and password before a medical procedure query can be made. The semantic module 126 may be configured to display the query results in a particular way when this particular user name and password are used. For example, if the user name and password belong to an oncologist, all of the information in the query results associated with oncology may be displayed first.

In other words, the query generation module 124 is configured to parse the medical procedure query and provide the queries to standards databases and/or medical procedure/results databases to obtain the requested information. The semantic module 126 is configured to obtain the results provided by the query generation module 124 and format the results in a user friendly format.

The learning module 122 may be configured to learn from previously run medical procedure queries and modify the query results accordingly. Thus, each time a user runs a medical procedure query the learning module 122 learns something and adjusts the results of the next query accordingly. For example, a user may make a first medical procedure query and the query results may be provided to the user. Responsive to the query results, the user may provide a similar, but modified medical procedure query. The learning module may be configured to recognize this pattern and adjust the results of the next query so as to reduce the likelihood that the user will have to make the second modified query. Furthermore, in some embodiments of the present invention, the learning module may be configured to direct specific questions to the user to obtain information that may be used to fine tune future query results. For example, the learning module may be configured to ask the user "how close were the query results to what you wanted (0 to 100 percent)?" The user may specify a percentage, which the learning module 122 may be configured to use to modify future query results. Accordingly, the learning module 122 may implicitly learn from the actions taken by users of the query engine as well as from answers to specific questions posed by the learning module 122 without departing from the scope of the present invention.

While the present invention is illustrated with reference to the semantic module 126, the query generation module 124 and the learning module 122 being application programs in FIG. 1, as will be appreciated by those of skill in the art, other configurations fall within the scope of the present invention. For example, rather than being application programs 154, these modules may also be incorporated into the operating system 152 or other such logical division of the data processing system 100. Furthermore, while the semantic module 126, the query generation module 124 and the learning module 122 are illustrated in a single data processing system, as will be appreciated by those of skill in the art, such functionality may be distributed across one or more data processing systems. Thus, the present invention should not be construed as limited to the configuration illustrated in FIG. 1, but may be provided by other arrangements and/or divisions of functions between data processing systems. For example, although FIG. 1 is illustrated as having various circuits/modules, one or more of these circuits may be combined without departing from the scope of the present invention.

Figure 2:
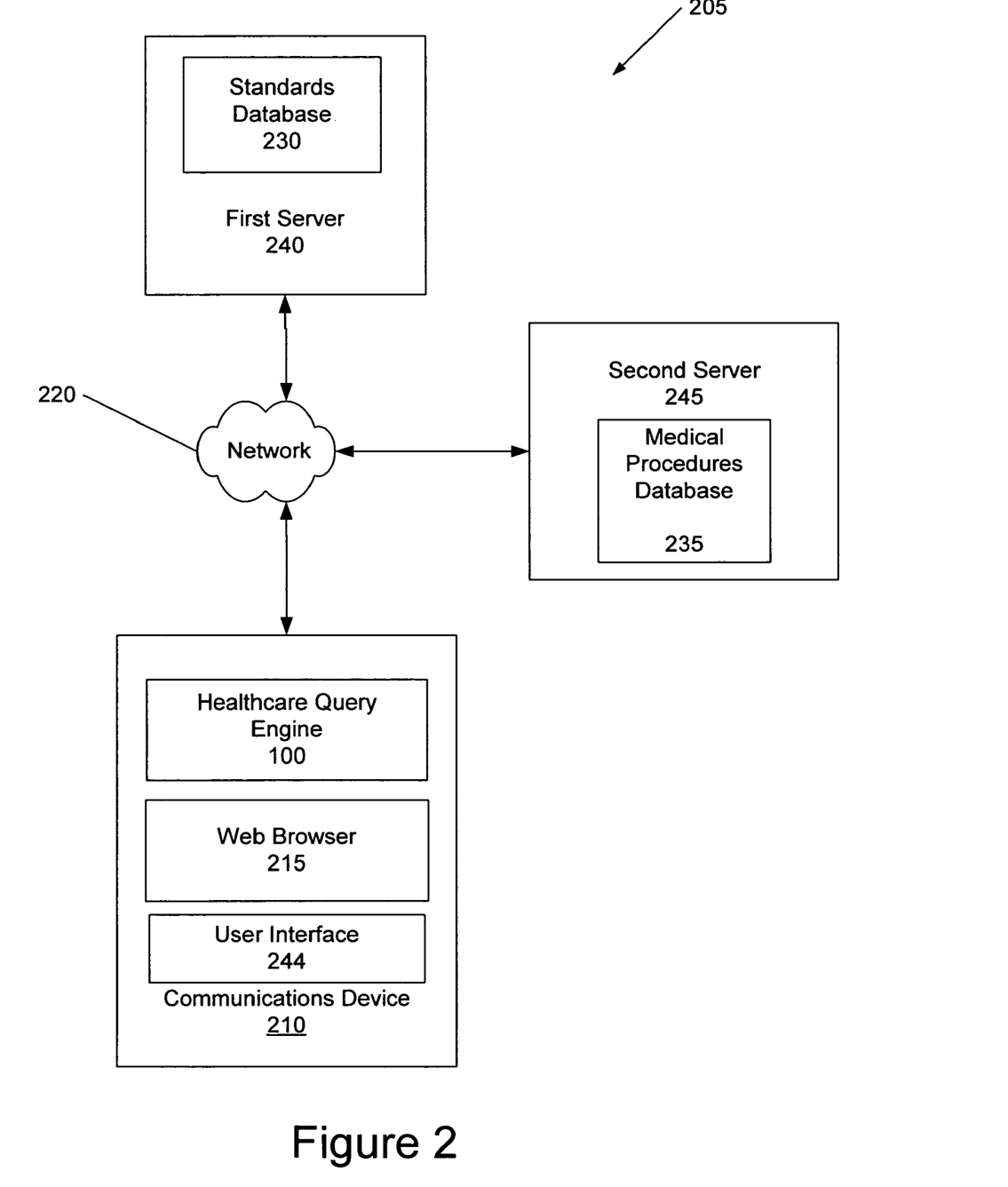
FIG. 2 is a block diagram illustrating an exemplary network environment for operations and devices according to some embodiments of the present invention.

Referring now to FIG. 2, an exemplary environment 205 for operations and devices according to some embodiments of the present invention will be discussed. As illustrated in FIG. 2, the environment 205 may include a communications device 210, a network 220, a first server 240 and a second server 245. As illustrated, the communications device 210 illustrated in FIG. 2 may include the healthcare query module 100 according to some embodiments of the present invention discussed above with respect to FIG. 1. For example, the application programs 154 discussed with respect to FIG. 1 could be included as part of the healthcare query module 100 of the communications device 210. The communications device 210 may be, for example, a laptop computer, a desktop computer, a personal data assistant (PDA), a web capable mobile terminal or any device capable of communicating with the network 220. The communications device 210 may include a user interface 244, which may be used to enter medical procedure queries according to some embodiments of the present invention, a web browser 215 that may be accessed through the user interface 244, and a healthcare query module 200 according to some embodiments of the present invention. As discussed above, the healthcare query module 100 may be configured to receive medical procedure queries about one or more patients as discussed above with respect to FIG. 1. The first server 240 may include a standards database 230 including medical standards, such as, CPT and HCPCS, local standards, insurance codes and journal articles as discussed above with respect to FIG. 1. The second server 245 may include a medical procedures database 235, which may include medical procedures performed and results thereof, such as lab results, images, physician's notes and the like as discussed above with respect to FIG. 1. The communications device 210 may communicate over the network 220, for example, the Internet, through a telephone line, a digital subscriber link (DSL), a broadband cable link, a wireless link or the like. The first and second servers 240 and 245 may also communicate over the network 220. Thus, the network 220 may convey data between the communications device 210 and the first and second servers 240 and 245.

It will be understood that although only a single standards database 230 and a single medical procedures database 235 are illustrated in FIG. 2, embodiments of the present invention are not limited to this configuration. For example, multiple standards databases and multiple medical procedures databases can be included in the environment 205 without departing from the scope of the present invention. For example, there may be a standards database corresponding to each of the current medical standards, each of the local standards and each medical journal.

Figure 3:
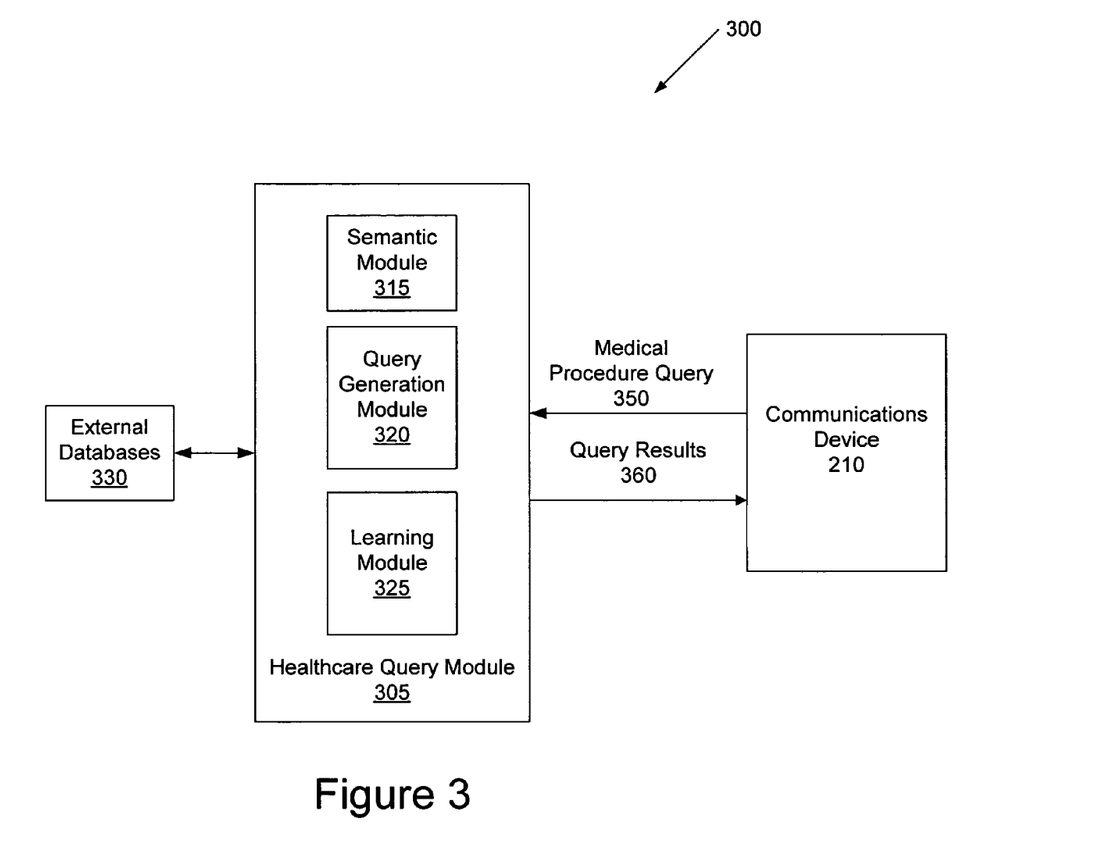
FIG. 3 is a block diagram illustrating data flows of a system including a healthcare query module according to some embodiments of the present invention.

Exemplary data flows of a system including a healthcare query module according to some embodiments of the present invention will be discussed with respect to FIG. 3. As illustrated in FIG. 3, the system 300 includes a communication device 210, a healthcare query module 305 and external databases 330. The communications devices 210 may include a user interface 244 and a web browser 215 as discussed above with respect to FIG. 2. The healthcare query module 305 may include the semantic module 315, the query generation module 320 and the learning module 325. It will be understood that the healthcare query module 305 may be provided in the communications device 210 as illustrated in FIG. 2 or be separate from the communications device 210 without departing from the scope of the present invention. The external databases 330 may include the standards and/or medical procedure databases as discussed above.

A user, for example, a doctor, may provide a medical procedure query 350 to the healthcare query module 305 according to some embodiments of the present invention. Before the healthcare query module 305 processes the medical procedure query 350, the healthcare query module 305 may verify a username and password provided by the doctor to determine the doctor's level of security clearance, i.e., which databases the doctor can access. Furthermore, in some embodiments of the present invention, the user (doctor) may also provide usage information at sign on, i e., information associated with the reason the doctor is accessing the information, such as research purposes or treatment purposes. The information available to the user may change significantly based on the usage information. In other words, the same user may have access to different information based on their current usage status, such as researcher or medical provider.

As discussed above, the medical procedure query 350 may be a discrete query or a more complicated semantic query. Once the username and password are verified and the medical procedure query 350 is received at the healthcare query module 305, the query generation module 320 may parse the query to determine what information has been requested. For example, the query generation module 320 may find a CPT code for mammogram in the medical procedure query 350. Thus, the query generation module 320 may request the equivalent standards code in HCPCS and the like from the standards databases (external databases 330). Once each of these codes has been identified, including outdated codes that have been given updated code names, the query generation module 320 may search the medical procedure databases that the doctor has clearance access to for each of these codes.

Once the results of this search are received by the query generation module 320, query results 360 may be provided directly to the doctor at the communications device 210. However, in some embodiments of the present invention, the query generation module 320 may provide the query results 360 to the semantic module 315 before providing the results to the doctor. For example, the semantic module 315 may be configured to format the query results in accordance with user preferences associated with the username and password. For example, if the doctor is an oncologist, all of the oncology related results may be provided first. Once the semantic module 315 has formatted the query results 360, the query results 396 may be provided to the doctor.

In some embodiments of the present invention, the doctor may receive the results and then provide a modified medical procedure query 350 responsive to the query results 360. This may indicate to the healthcare query module 305 that the doctor was not totally satisfied with the query results 360. Thus, the learning module 325 may be configured to recognize a difference between the first and second queries and modify the next set of query results based on what it learned from the difference. Thus, each time a query is made, the learning module 325 may learn something, which may be used to improve the query results associated with future medical procedure queries. In some embodiments of the present invention, the learning module 325 may be further configured to ask specific questions of the user, the answers to which can be used to fine tune future query results.

It will be understood that the exemplary operations discussed with respect to FIG. 3 are provided for exemplary purposes only and, therefore, embodiments of the present invention should not be limited to the specifics of the example discussed herein.

Figure 4:
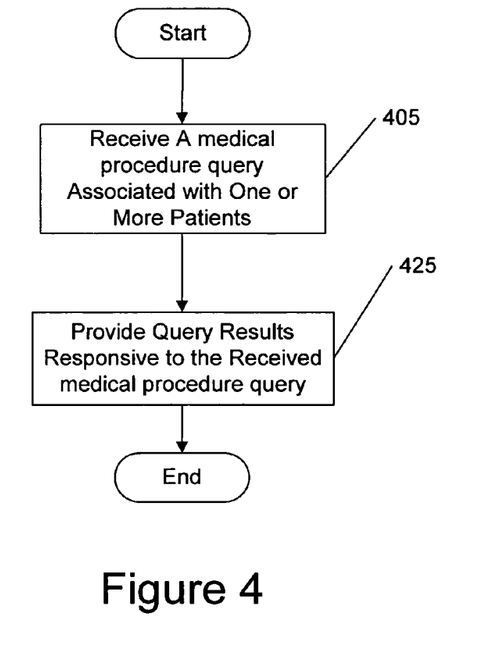
FIGS. 4 through 6 are flowcharts illustrating operations according to various embodiments of the present invention.

Operations according to various embodiments of the present invention will now be discussed with respect to the flowcharts of FIGS. 4 through 6. Operations for synthesizing medical procedures stored in healthcare databases begin at block 405 by receiving a medical procedure query associated with a single patient or a group of patients. The medical procedure query can be, for example, a discrete query and/or a semantic query. Query results are provided responsive to the medical procedure query (block 425). The query results include medical procedure information from multiple sources, for example, multiple hospital databases, that are expressed in multiple standards formats, for example, CPT and HCPCS and the like. It will be understood that the medical procedure query may only specify a single standard code and the additional codes may be located according to some embodiments of the present invention.

Figure 5:
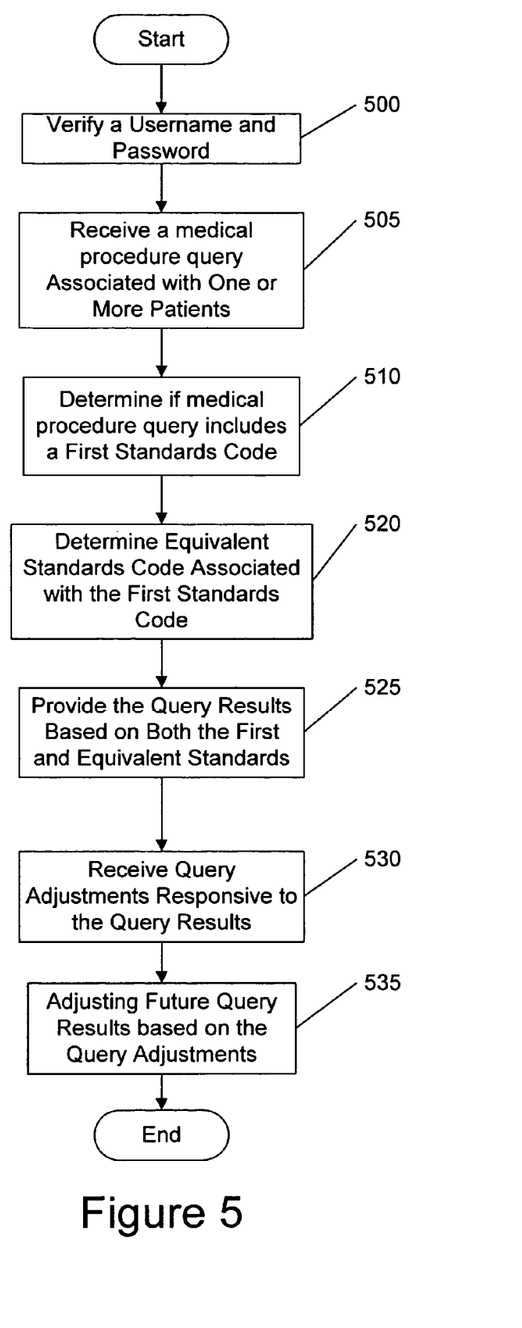

Referring now to FIG. 5, operations begin at block 500 by verifying a username and password. Each user, for example, doctor or researcher, may have a unique username and level of security clearance. The level of security clearance may determine which information can be accessed by the user of the associated username and password. A medical procedure query associated with a single patient or a group of patients is received if the username and password are verified (block 505). It is determined if the medical procedure query includes a first standards code in conformance with a first standard therein (block 510). For example, the medical procedure query may include the CPT code for open heart surgery. If it is determined that the medical procedure query includes a first standards code (block 510), equivalent standards codes to the first standards code are determined in conformance with at least one second standard, different from the first standard (block 520). For example, the corresponding HCPCS etc. codes for open heart surgery may be determined. The query results are provided based on both the first standards code and the equivalent standards codes (block 525). Thus, all (or more than one) the open heart surgery codes may be searched and the results with respect to each may be provided even though only a single code in conformance with a single standard is provided in the medical procedure query.

Query adjustments may be received from the user responsive to the query results provided (block 530). This may indicate that the user was not completely satisfied with the query results. Thus, future query results may be adjusted based on the received query adjustments (block 535). The future query results may also be adjusted based on user's answers to explicit questions without departing from the scope of the present invention.

Figure 6:
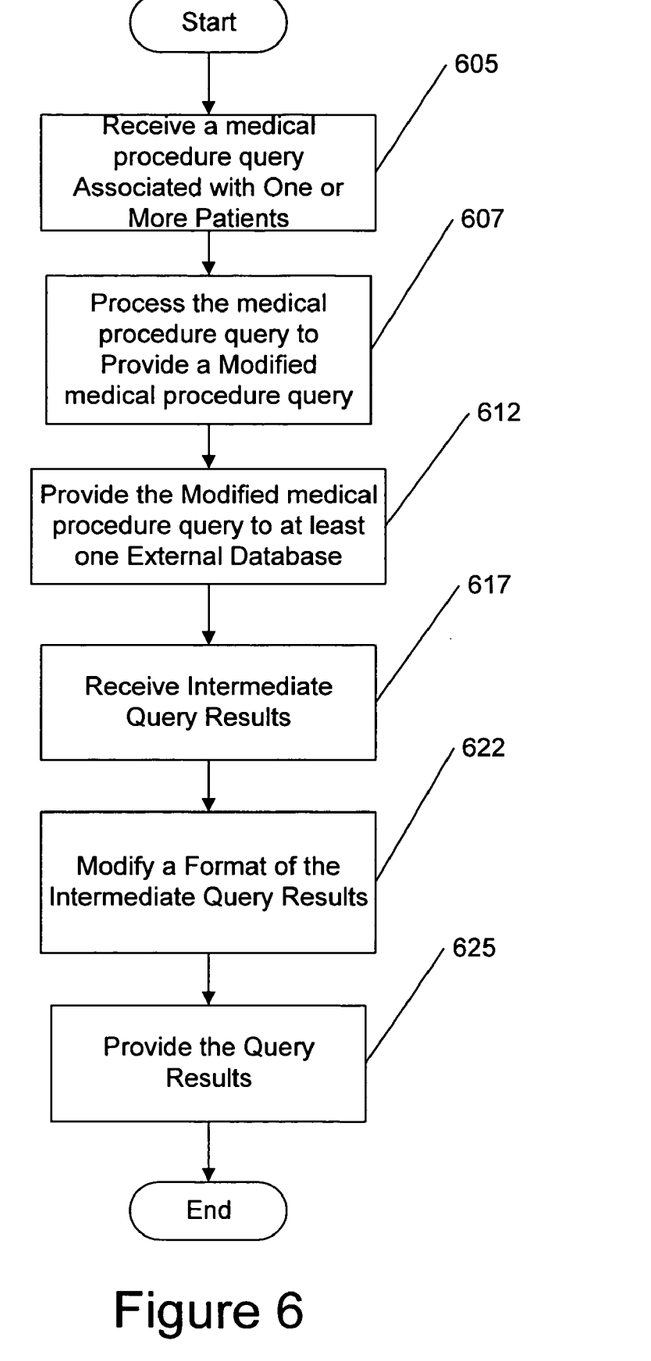

Referring now to FIG. 6, operations begin at block 605 by receiving a medical procedure query associated with a single patient or a group of patients. The medical procedure query may be processed to generate at least one modified medical procedure query that can be provided to external databases to obtain the query results (block 607). The at least one modified medical procedure query may be provided to at least one standards database and/or at least one medical procedures database (block 612). Intermediate query results may be received from the at least one standards database and/or the at least one medical procedures database (block 617). A format of the intermediate query results may be modified before providing the query results to a user (block 622). In some embodiments of the present invention, the query results may be modified/formatted based on a user profile and/or information obtained from previously received medical procedure queries and/or associated with a username and password. For example, if the user is an oncologist, all of the oncology related results may be provided first.

It will be understood that the circuits and other means supported by each block and combinations of blocks can be implemented by special purpose hardware, software or firmware operating on special or general purpose data processors, or combinations thereof. It should also be noted that, in some alternative implementations, the operations noted in the blocks may occur out of the order noted in the figures. For example, two blocks shown in succession may, in fact, be executed substantially concurrently, or the blocks may sometimes be executed in the reverse order.

Many alterations and modifications may be made by those having ordinary skill in the art, given the benefit of present disclosure, without departing from the spirit and scope of the invention. Therefore, it must be understood that the illustrated embodiments have been set forth only for the purposes of example, and that it should not be taken as limiting the invention as defined by the following claims. The following claims are, therefore, to be read to include not only the combination of elements which are literally set forth but all equivalent elements for performing substantially the same function in substantially the same way to obtain substantially the same result. The claims are thus to be understood to include what is specifically illustrated and described above, what is conceptually equivalent, and also what incorporates the essential idea of the invention.

That which is claimed is:

1. A computer-implemented method of synthesizing medical procedures stored in healthcare databases, the method comprising:
   receiving at a computer a medical procedure query associated with a single patient or a group of patients; and
   a processor of the computer providing returned query results responsive to the medical procedure query, the returned query results including medical procedures from multiple sources that are expressed in multiple standards formats and are associated with the single patient or the group of patients, wherein the providing returned query results comprises:
   determining if the medical procedure query includes a first standards code in conformance with a first standard;
   determining equivalent standards codes to the first standards code in conformance with at least one second standard, different from the first standard, if it is determined that the medical procedure query includes a first standards code; and providing the returned query results based on both the first standards code and the equivalent standards codes of the at least one second standard;
wherein the providing returned query results is preceded by processing the received medical procedure query to generate at least one modified medical procedure query that can be provided to external databases to obtain intermediate query results;
providing the at least one modified medical procedure query to one or more of at least one standards database and at least one medical procedure/results database;
receiving the intermediate query results from the one or more of the at least one standards database and the at least one medical procedure/results database; and
modifying a format of the intermediate query results to generate the returned query results before providing the returned query results to a user, wherein the intermediate query results are returned in response to the at least one modified medical procedure query.

2. The method of claim 1, wherein said receiving is preceded by verifying a username and password associated with the username and wherein said receiving further comprises receiving the medical procedure query only if the username and password are verified.

3. The method of claim 2, wherein each username and associated password is associated with a level of security clearance, the level of security clearance determining which information can be accessed by a user of the associated username and password.

4. The method of claim 1, further comprising receiving query adjustments responsive to the returned query results.

5. The method of claim 4, further comprising adjusting future query results based on the received query adjustments.

6. The method of claim 1, wherein the received medical procedure query comprises a discrete query or a semantic query.

7. The method of claim 1, wherein modifying the format further comprises modifying the format based on a user profile and/or information obtained from previously received medical procedure queries.

8. A system for synthesizing medical procedure information stored in healthcare databases, the system comprising:
a healthcare query module configured to receive a medical procedure query associated with a single patient or a group of patients and provide returned query results responsive to the medical procedure query, the returned query results including medical procedures from multiple sources that are expressed in multiple standards formats and are associated with the single patient or the group of patients; and
wherein the healthcare query module comprises a query generation module, the query generation module being configured to:
determine if the medical procedure query includes a first standards code in conformance with a first standard;
determine equivalent standards codes to the first standards code in conformance with at least one second standard, different from the first standard, if it is determined that the medical procedure query includes a first standards code;
provide the returned query results based on both the first standards code and the equivalent standards codes of the at least one second standard
process the received medical procedure query to generate at least one modified medical procedure query that can be provided to external databases to obtain intermediate query results;
provide the at least one modified medical procedure query to one or more of at least one standards database and at least one medical procedure/results database;
receive the intermediate query results from the one or more of the at least one standards database and the at least one medical procedure results/database; and
wherein the healthcare query module further comprises a semantic module, the semantic module being configured to modify a format of the intermediate query results to generate the returned query results before providing the returned query results to a user, wherein the intermediate query results are returned in response to the at least one modified medical procedure query.

9. The system of claim 8, wherein the healthcare query module is further configured to verify a username and password associated with the username before receiving the medical procedure query and receive the medical procedure query only if the username and password are verified.

10. The system of claim 9, wherein each username and associated password is associated with a level of security clearance, the level of security clearance determining which information can be accessed by a user of the associated username and password.

11. The system of claim 8, wherein the healthcare query module further comprises a learning module, the learning module being configured to receive query adjustments responsive to the returned query results.

12. The system of claim 11, wherein the learning module is further configured to adjust future query results based on the received query adjustments.

13. The system of claim 8, wherein the received medical procedure query comprises a discrete query or a semantic query.

14. The system of claim 8, wherein the semantic module is further configured to modify the format based on a user profile and/or information obtained from previously received medical procedure queries.

15. A computer program product for synthesizing medical procedure information stored in healthcare databases, the computer program product comprising:
a computer readable storage medium having computer readable program code embodied in said medium, the computer readable program code comprising:
computer readable program code configured to receive a medical procedure query associated with a single patient or a group of patients; and
computer readable program code configured to provide returned query results responsive to the medical procedure query, the returned query results including medical procedures from multiple sources that are expressed in multiple standards formats and are associated with the single patient or the group of patients;
wherein the computer readable program code configured to provide returned query results comprises:
computer readable program code configured to determine if the medical procedure query includes a first standards code in conformance with a first standard;
computer readable program code configured to determine equivalent standards codes to the first standards code in conformance with at least one second standard, different from the first standard, if it is determined that the medical procedure query includes a first standards code;
computer readable program code configured to provide the returned query results based on both the first standards code and the equivalent standards codes of the at least one second standard;

computer readable program code configured to process the received medical procedure query to generate at least one modified medical procedure query that can be provided to external databases to obtain intermediate query results;

computer readable program code configured to provide the at least one modified medical procedure query one or more of at least one standards database and at least one medical procedure/results database;

computer readable program code configured to receive the intermediate query results from the one or more of the at least one standards database and the at least one medical procedure/results database; and computer readable program code configured to modify a format of the intermediate query results to generate the returned query results before providing the returned query results to a user, wherein the intermediate query results are returned in response to the at least one modified medical procedure query.

16. The computer program product of claim 15, further comprising computer readable program code configured to verify username and password associated with the username, wherein the computer readable program code configured to receive further comprises computer readable program code configured to receive the medical procedure query only if the username and password are verified.

17. The computer program product of claim 16, wherein each username and associated password is associated with a level of security clearance, the level of security clearance determining which information can be accessed by a user of the associated username and password.

18. The computer program product of claim 15, further comprising computer readable program code configured to receive query adjustments responsive to the returned query results.

19. The computer program product of claim 18, further comprising computer readable program code configured to adjust future query results based on the received query adjustments.

20. The computer program product of claim 15, wherein the received medical procedure query comprises a discrete query or a semantic query.

21. The computer program product of claim 15, wherein the computer readable program code configured to modify the format further comprises computer readable program code configured to modify the format based on a user profile and/or information obtained from previously received medical procedure queries.

* * * * *